(12) United States Patent
Reifman et al.

(10) Patent No.: US 6,425,875 B1
(45) Date of Patent: Jul. 30, 2002

(54) METHOD AND DEVICE FOR DETECTION OF A TOOTH ROOT APEX

(75) Inventors: Mark Reifman; Abraham Taub, both of Rishon Lezion; Michael Yakoby, Kfar Saba, all of (IL)

(73) Assignee: Forum Engineering Technologies (96) Ltd., Rishon Lezion (IL)

( * ) Notice: Subject to any disclaimer, the term of this patent is extended or adjusted under 35 U.S.C. 154(b) by 0 days.

(21) Appl. No.: 09/473,229

(22) Filed: Dec. 27, 1999

(51) Int. Cl.[7] .......................... A61B 5/103; A61B 5/117
(52) U.S. Cl. ...................................... 600/590
(58) Field of Search .................... 600/590, 587, 600/589; 433/27, 224, 32, 72

(56) References Cited

U.S. PATENT DOCUMENTS

| | | | |
|---|---|---|---|
| 4,447,206 A | 5/1984 | Ushiyama | 433/27 |
| 5,063,937 A | 11/1991 | Ezenwa et al. | 128/723 |
| 5,080,586 A | 1/1992 | Kawai | 433/32 |
| 5,096,419 A | 3/1992 | Kobayashi et al. | 433/72 |
| 5,112,224 A * | 5/1992 | Shirota | 433/27 |
| 5,759,159 A | 6/1998 | Masreliez | 600/547 |

FOREIGN PATENT DOCUMENTS

WO    WO 98/12983    4/1998    ........... A61C/19/04

OTHER PUBLICATIONS

International Search Report for International Application No. PCT/IL 00/00863, mailed on May 7, 2001.

* cited by examiner

Primary Examiner—John P. Lacyk
Assistant Examiner—Brian Szmal
(74) Attorney, Agent, or Firm—Fitch, Even, Tabin & Flannery

(57) ABSTRACT

A device for locating an apex of a root canal of a tooth comprises a first electrode having a conductive probe with a tip adapted for insertion into the root canal, and a second electrode configured to electrically contact a patient's body. The device includes a voltage generator which provides AC test voltage signal, a AC voltage driver with an internal output impedance, and a voltage detector coupled to the electrodes to detect an AC voltage across the first and second electrodes. An electronic controller coupled to the voltage detector calculates the test scores, determines the position of the probe tip on the basis of the test score values, and informs the user of the position of the probe tip in the canal. The position of the probe tip in the root canal is indicated on a display by a marker.

61 Claims, 5 Drawing Sheets

METHOD AND DEVICE FOR DETECTION OF A TOOTH ROOT APEX

FIELD OF THE INVENTION

The present invention relates to dental equipment, and more particularly, to measuring equipment for dental endodontics.

BACKGROUND OF THE INVENTION

In root canal therapy, a dental probe, such as a reamer or file, is inserted into the canal and manipulated to remove undesired material A flexible filler substance is then placed in the root canal that is sealed with a rigid material. If the canal is not completely cleaned before filling and sealing, debris left inside the canal can prevent proper healing. The probe must therefore be inserted all the way to the apex of the root canal during cleaning to remove all debris. On the other hand, if the probe is inserted too deeply, the tool penetrates the jaw tissue, causing swelling and unnecessary trauma for the patient. It is therefore essential to precisely determine when the probe tip is located at the root canal apex so that the canal can be cleaned fully without excessive trauma to the patient.

Locating the apex is difficult because the narrow canal does not provide a clear viewing path and fluids can partially fill the canal. In one method, the probe is inserted into the canal and the tooth is x-rayed. In the x-ray image, the metal probe contrasts with the surrounding tooth and body tissue so that the positions of the probe tip and the apex can be compared. If the probe tip is not at the apex, it is inserted deeper into the canal and a new x-ray image is obtained. This method is unreliable, time-consuming, costly, and entails excessive exposure of the patient to X-ray radiation.

It is also known to locate a root apex by inserting a conductive probe into the root canal and placing an electrode in contact with the patient's body, usually in or near the mouth. As the probe is moved through the canal towards the apex, electrical measurements across the probe and electrode are made. For example, U.S. Pat. No. 5,063,937 discloses an apex detector utilizing an AC signal at a single frequency. The probe tip is determined to be at the apex when the result of a calculation based upon these measurements is within a predetermined range. However, methods that utilize a single frequency AC signal for apex positioning are not accurate in the vicinity of the apex.

U.S. Pat. No. 5,096,419 to Kobayashi et al., discloses locating the apex by making impedance measurements at two frequencies as the probe is moved towards the apex. A detector determines that the probe tip as at the apex when the ratio of the two impedance measurements is within a predetermined range. U.S. Pat. No. 5,759,159 to Masreliez discloses locating a root apex based upon the amplitude or phase of voltage measurements across the probe and the electrode as the probe is moved towards the apex. However, amplitude and phase measurements are affected by inevitable signal distortion Moreover, the multiple frequency methods are accurate only near the apex and cannot indicate the probe position before the probe tip approaches the apex region.

With prior art apex locators, whether single or multiple frequency, the frequency or frequencies of the test signals, as well as the internal impedance, of the devices are fixed by the manufacturer, and cannot be changed during operation. However, the electrical parameters of the tissues of the root canal and jaw may vary significantly from patient to patient, from one tooth to another of the same patient, and even from one canal to another in the same tooth. Fixed test frequencies and internal impedance of the device obviously cannot be optimal for all cases. Hence, the precision afforded by these devices is limited.

SUMMARY OF THE INVENTION

In the following description and set of claims, two explicitly described, calculable or measurable variables are considered equivalent to each other when the two variables are substantially proportional to each other.

The present invention provides a method and device for locating the apex of a root canal. The device comprises two electrodes. A conductive probe inserted into a root canal forms the first electrode. A second electrode contacts the patient's body, typically in the mouth area. An AC voltage test signal $V_g$ is applied to a driver having an internal output impedance $Z_o$. The internal output impedance of the device and the impedance of the tissues between the two electrodes form a parametric voltage divider. The test signal $V_g$ may be a single frequency or a multi-frequency signal. The internal output impedance $Z_o$ may be kept constant during the measurements, or be made to vary. As the probe tip is moved through the canal towards the apex, voltage measurements $V_i$ across the probe and electrode are continuously made and a microprocessor calculates one or more test scores based upon the voltage measurements. The current position of the probe in the canal is then determined on the basis of the test scores.

In the following description and set of claims, the portion of the root canal near the apex is referred to as "region B" of the canal. The rest of the canal is referred to herein as "region A" of the canal. Determining the position of the probe tip may simply involve determining whether the tip is in region A, in region B, at the apex, or in the jaw tissue In this case, as the probe tip is moved towards the apex, the test score is compared to a first numerical value. When the test score is less than the first numerical value, the user is informed that the tip is in region A. When the test score first equals the first numerical value, the user is informed that the tip is in region B. When the test score first reaches a second numerical value, the user is informed that the probe tip is at the apex. When the test score exceeds the second numerical value, the user is informed that the tip has passed the apex and entered the jaw tissue. The position of the probe tip in the canal may be indicated to the user on a graphical or numerical display, or by means of a sensible signal such as a bell.

Alternatively, determining the position of the probe tip may involve continuously determining the distance of the probe tip from the apex. In this case, the location of the probe in the canal may be displayed continuously on a graphical or numerical display starting from the first insertion of the probe into the canal until the probe tip has reached the apex.

The test score may involve, for example, the root mean square (RMS) of the voltage measurements $V_i$. Unlike phase and amplitude measurements, RMS measurements are essentially unaffected by signal distortion. In one embodiment, a test signal $V_g$ having a single frequency $f_1$ is used while the internal output impedance $Z_o$ is kept constant, for example 3 Kohm. $V_g(f_1)$ may be, for example, 30–50 mV. As the probe is moved in the canal, the novel test score $L_1 = S_1(RMS(V_i(f_1,P_0)) - RMS(V_i(f_1,P_k)))$ is calculated where $S_1$ is a scaling factor, and $P_0$ and $P_k$ designate, respectively, the initial and current probe positions inside the root canal. S1 may be, for example, about 75. This embodiment may make use of the unexpected finding that when the tip is in region A, the test score $L_1$ is essentially a linear function of the probe tip position in the canal.

In another embodiment, a test signal $V_g$ having two frequencies $f_1$ and $f_2$ is used while the internal output impedance $Z_o$ is kept constant. $f_1$ and $f_2$ may be, for example, in the 400–500 Hz and 8–10 kHz ranges, respectively As the probe is moved in the canal, the novel test score $D_1 = S_2(RMS(V_i(f_1, P_k)) - RMS(V_i(f_2, P_k)))$ is calculated where $S_2$ is another scaling factor. This embodiment may make use of the unexpected finding that in region B, $D_1$ is a linear function of the distance between the probe tip and the apex.

In a most preferred embodiment, the test scores $L_1$ and $D_1$ are used simultaneously. The test score $L_1$ is used to locate the probe tip when it is in region A. When $L_1$ first satisfies a predetermined condition that may depend upon the simultaneously obtained test score $D_1$, the probe tip has passed from region A to region B. The condition may be, for example that $L_1 = D_1(P_k) - D_1(P_0)$. The test score $D_1$ is then used to determine the probe tip position. When the value of the test score $D_1$ exceeds a first predetermined threshold T1, the probe tip is close to the apex, for instance, 1 mm from the apex. When the value of the score reaches a second predetermined threshold T2, the probe tip is at the apex. When value of the test score exceeds the second predetermined threshold T2, the probe tip has passed the apex. T1 and T2 may be, for example, 0.196 V, and 0.294V, respectively.

In another embodiment, $V_i$ measurements are initially obtained using a testing signal $V_g$ having two frequencies $f_1$ and $f_2$ and one or more test scores calculated. $V_i$ measurements are then performed using a testing signal $V_g$ having new frequencies $f_3$ and $f_4$ better suited to the specific case that are determined based upon the test scores obtained with the initial pair of frequencies. For example, initial frequencies $f_1$ and $f_2$ of 1 kHz and 8 kHz respectively may be selected. If a test score obtained using the frequencies $f_1$ and $f_2$ is less than a predetermined value, the frequencies are decreased. If the test scores exceeds this value, the frequencies are increased. The process may be repeated dynamically to arrive at an optimal pair of frequencies for the particular canal.

In yet another embodiment, voltage measurements are made at a fixed frequency but at two different output impedances $Z_1$ and $Z_2$ of the device. One or more test scores are calculated that may involve, for example, the amplitude, phase, or RMS of the voltage measurements. For example, the test scores $L_2 = S_1(RMS(V_1(Z_1, P_0)) - RMS(V_1(Z_1, P_k)))$ and $D_2 = S_2(RMS(V_i(Z_1, P_k)) - RMS(V_i(Z_2, P_k)))$ may be used. The test score $L_2$ is used to locate the probe tip when it is n region A. When $L_2$ first satisfies a predetermined condition that may depend upon the simultaneously obtained test score $D_2$, the probe tip has passed from region A to region B. The test score $D_2$ is then used to determine the probe tip position. When the value of the test score $D_2$ exceeds a first predetermined threshold T1, the probe tip is close to the apex, for instance, 1 mm from the apex. When the value of $D_2$ reaches a second predetermined threshold T2, the probe tip is at the apex. When value of the test score exceeds the second predetermined threshold T2, the probe tip has passed the apex. T1 and T2 may be, for example, 0.196 V, and 0.294V, respectively.

In either embodiment the position of the probe tip in the canal may be displayed graphically and/or numerically to a user as the probe is moved in the canal. For example, the display may include an illustration of a tooth canal and a marker may; be introduced into the illustration indicating the position of the probe tip in the canal. Once the score $D_1$ or $D_2$ respectively exceeds a first threshold T1 indicating that the probe tip is close to the apex, the scale of the graphic display may be enlarged to provide a more accurate indication of position of the probe tip near the apex. A sensible signal such as a light or a bell may also be used to indicate that the probe is near or at the apex. A visual and/or audio signal may indicate that the probe tip has passed the apex. The invention thus provides a device for locating an apex of a root canal of a tooth, the root canal having a region A and a region B, comprising:

a a first electrode, the first electrode including a conductive probe adapted for insertion into the root canal, the probe having a tip;

b a second electrode configured to electrically contact a patient's body;

c an AC voltage generator configured to provide an AC test voltage signal $V_g$ having one or more frequencies;

d an AC voltage driver being an interface between the voltage generator and the electrodes;

e a voltage detector coupled to the first and second electrodes, the voltage detector being operative to detect an AC voltage $V_i$ across the first and second electrodes;

f an electronic controller coupled to the voltage detector, the controller carrying out the steps of:

fa calculating one or more test scores, the one or more test scores each having a value that is a function of $V_i$;

fb determining, on the basis of the one or more test score values, the position of the probe tip in the canal; and fc informing a user of the position of the probe tip in the canal.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

Figure 1:
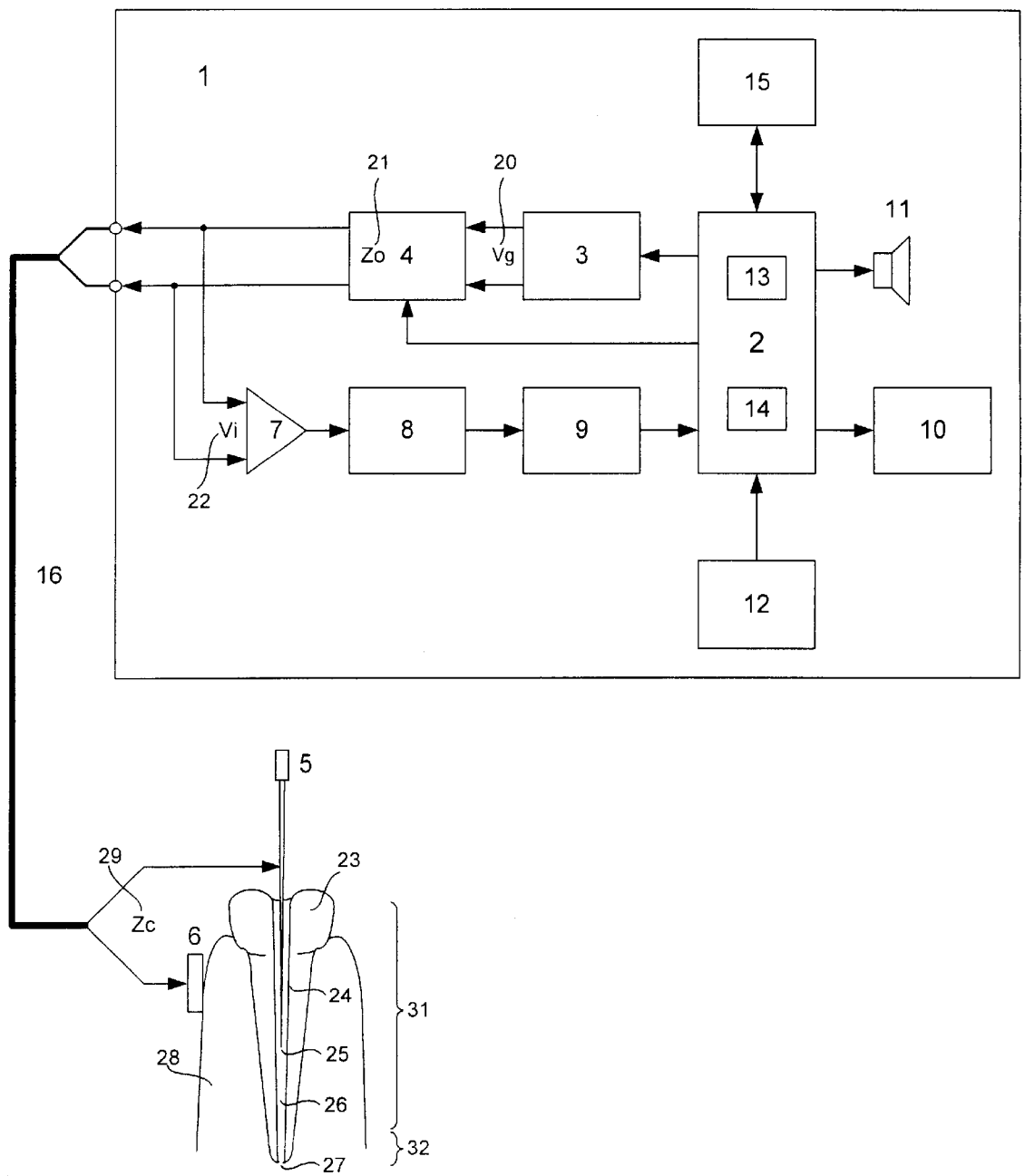
FIG. 1 shows an apical position detector according to one embodiment of the invention.

Referring first to FIG. 1, an apex detector, generally indicated 1, in accordance with one embodiment of the invention is shown that includes a microcontroller 2, signal generator 3, output driver 4, amplifier 7, RMS to DC converter 8, analog to digital converter 9, display 10, audio transducer 11 and keyboard 12. The apex detector 1 is connected to a conductive canal probe 5 and a lip electrode 6 via flexible cable 16 of sufficient length. The microcontroller 2 controls the operation of the apex detector 1 according to a computer program stored in a nonvolatile program memory 13 located in the microcontroller 2. The memory 13 may also contain a series of threshold values and other parameters that are accessed by the microcontroller 2 during operation. Random access memory (RAM) 14 located in the microcontroller 2 is used for temporary storage of data during the operation of the apex detector 1.

The apex detector 1 may optionally include a non-volatile EEPROM or FLASH memory 13 for storing user-defined parameters inputted to the microcontroller 2 by means of the keyboard 12. Memories 13 and 14 are not erased in the absence of a supply power.

Referring still to FIG. 1, the canal probe 5 is inserted into a canal 24 of a tooth 23. The lip electrode 6 is configured to contact the tissues of the mouth. The root canal 24 is divided into region A 31 and region B 32. The microcontroller 2 drives the signal generator 3 and optionally controls a variable output impedance $Z_o$ 21 of the driver 4. In response, the signal generator 3 produces an analog testing signal $V_g$ 20 that may be, for example, a sine wave with peak amplitude of 40 mV. The test signal 20 is applied to the electrodes 5 and 6 via output driver 4 and cable 16.

The measured region 26 of the canal 24 extends from the tip 25 of the canal probe 5 to the root apex 27. Jaw tissue 28 surrounds the tooth 23. The length of the measured region 26 depends upon the depth to which the canal probe 5 is inserted in to the canal 24. The impedance $Z_c$ 29 of the tissues between the probe tip 25 and the lip electrode 6 depends upon the length of the measured region 26. The voltage drop $V_i$ 22 where $V_i = V_g Z_c / (Z_o + Z_c)$, across the electrodes 5 and 6 is amplified by the amplifier 7 and the amplified signal is inputted to the RMS to DC converter 8. The signal is then digitized by the analog to digital converter 9 and inputted to the microcontroller 2.

The microcontroller 2 calculates one or more test scores based upon one or more $V_i$ measurements. When a test score involving two or more frequencies is used, for example, the test score $D_1$, a multiple frequency test voltage $V_g$ must be used. In this case the response voltage measurements $V_i$ are separated into their spectral components by the microcontroller 2. More preferably, however, a single frequency test signal $V_g$ is used that rapidly alternates among the different frequencies. Two or more $V_1$ measurements at different $V_g$ frequencies can be made within sufficiently short time period in which the position of the probe tip inside the root canal essentially does not change.

Figure 2:
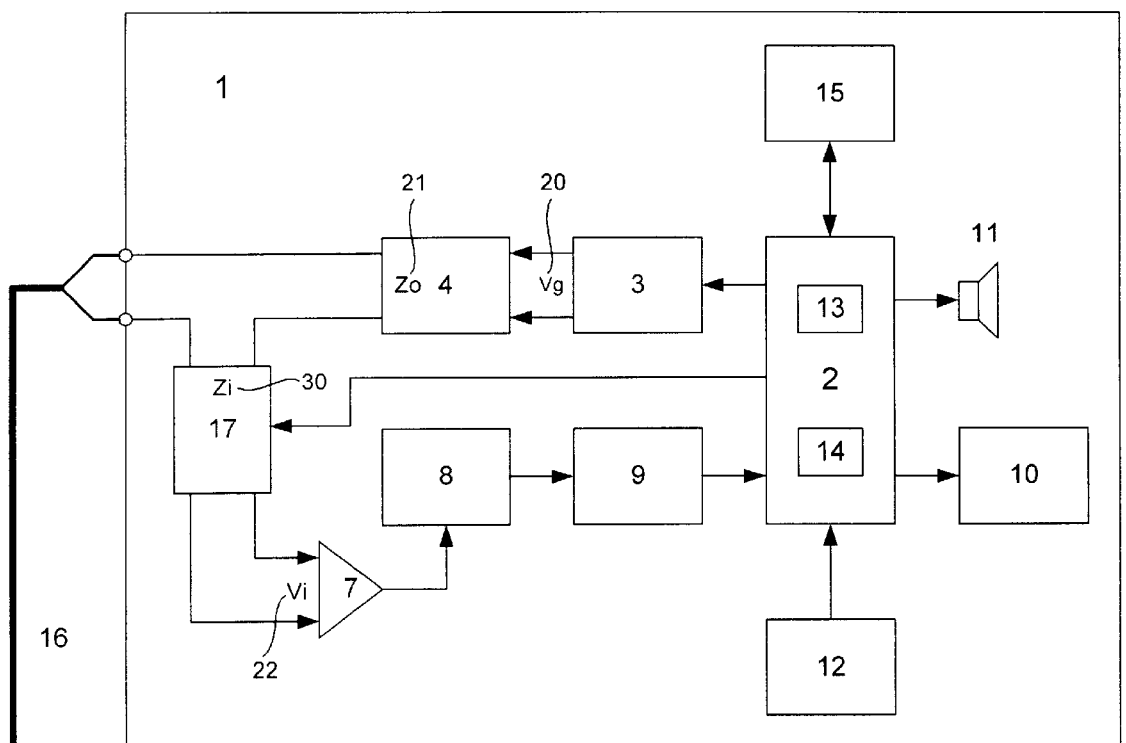
FIG. 2 shows an apical position detector according to another embodiment of the invention.
Figure 2:
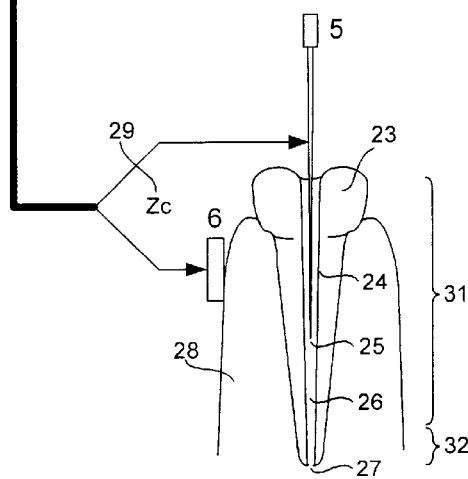

The microcontroller 2 then determines the position of the probe tip 25 in the root canal 24 based upon the test scores. Determining the position of the probe tip may simply involve determining whether the tip is far from the apex, near the apex or at the apex. Alternatively, determining the position of the probe tip may involve continuously determining the advance of the probe tip 25 in the canal or the distance of the probe tip from the apex. In either case, the position of probe is tip 25 is indicated to the user by the display 10 and/or the audio transducer 11. FIG. 2 shows another embodiment of the invention. The embodiment of FIG. 2 has several components in common with the embodiment of FIG. 1, and identical components in FIGS. 1 and 2 are designated by the same numeral. In the embodiment of FIG. 2, the microcontroller 2 controls a variable input impedance $Z_i$ 30 of input interface 17.

When voltage measurements are carried out using a test voltage $V_g$ 20 having a single frequency with two or more values of either the output impedance $Z_o$ 21 of the driver 4 (FIG. 1), or the input impedance $Z_i$ 30 of the input interface 17 (FIG. 2), the impedance 21 or 30 is varied by microcontroller 2. For example, the impedance $Z_o$ 21 of the output driver 4 may alternate between two impedance values $Z_1$ and $Z_2$ where $Z_1$ is a resistive impedance of about 3 kOhm and $Z_2$ is a capacitor of about 20 nF connected serially to resistor of about 3 kOhm. $V_i$ 22 is measured for each output impedance $Z_1$ and $Z_2$. The microcontroller 2 then calculates one or more test scores involving the measured $V_i(Z_1)$ and $V_i(Z_2)$. For example, in region A, $L_2$ or the amplitude or phase of $V_i(Z_1)$ may be used. In region B, $D_2$, or $V_i(Z_1)/V_i(Z_2)$ may be used as a test score. When $D_2$ is used as the test score, the probe tip is close to the apex, for example, about 1 mm from the apex, when $D_2$ exceeds a first predetermined threshold T1 that may be, for example, 0.196 V. When $D_2$ reaches a second threshold T2, for example, 0.294V, the probe tip as at the apex. When $D_2$ has exceeds the threshold T2, the probe tip has passed the apex and entered the jaw tissue.

Figure 3:
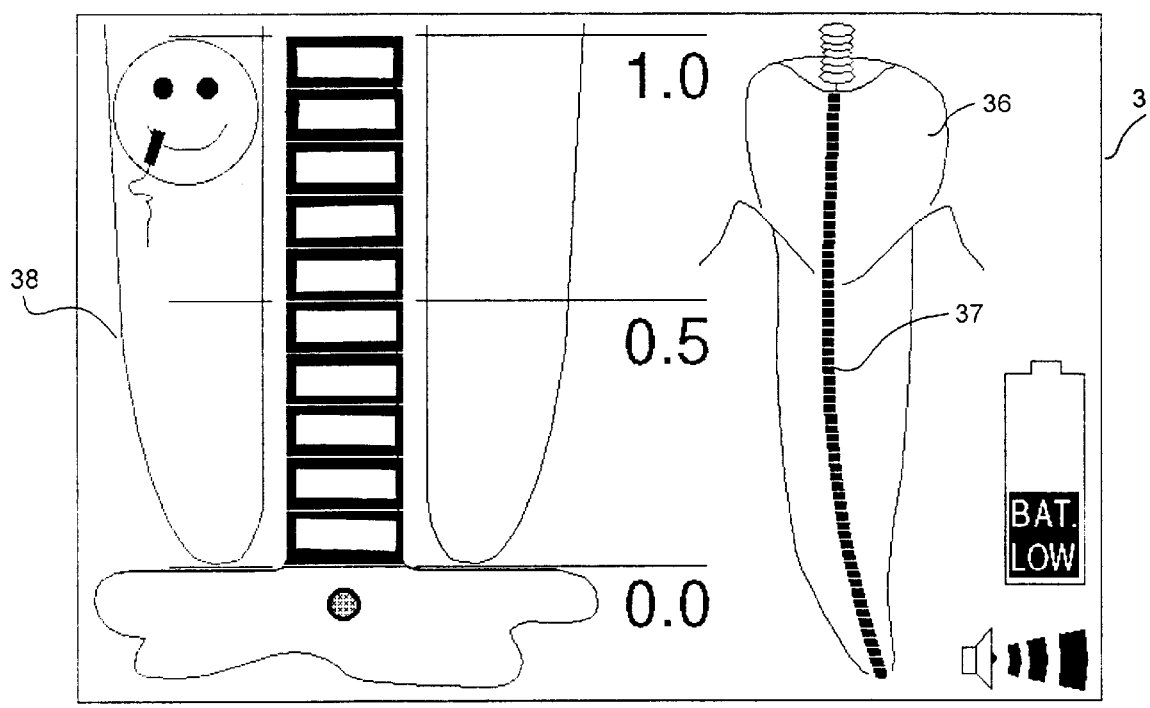
FIG. 3 shows a graphic display of an apical position detector according to one embodiment of the invention.

FIG. 3 shows a graphical display, generally indicated 35 that may be used in accordance with the invention. The display includes an illustration of a tooth 36 that is used to depict the probe tip 25 position when the probe tip 25 is located in region A 31 (FIGS. 1 and 2). The root canal 24 is indicated by a sequence of LEDs 37. When the probe tip 25 is in region A, one or more of the liquid crystal diode (LCD) segments are turned on in LCD sequence 37 indicating the position of probe tip 25 in the canal 24. The display also includes an illustration of a canal in the apex region 38 that is used to depict the probe tip 25 position when the probe tip 25 is located in region B 32. The root canal 24 in region B 32 is indicated by a sequence of LCDs 39. When the probe tip 25 is in region B 32, one or more of the LCDs are turned on in LED sequence 39 indicating the position of probe tip 25 in the region B 32 at a higher resolution than when the probe tip 25 is in the region A 31.

Figure 4:
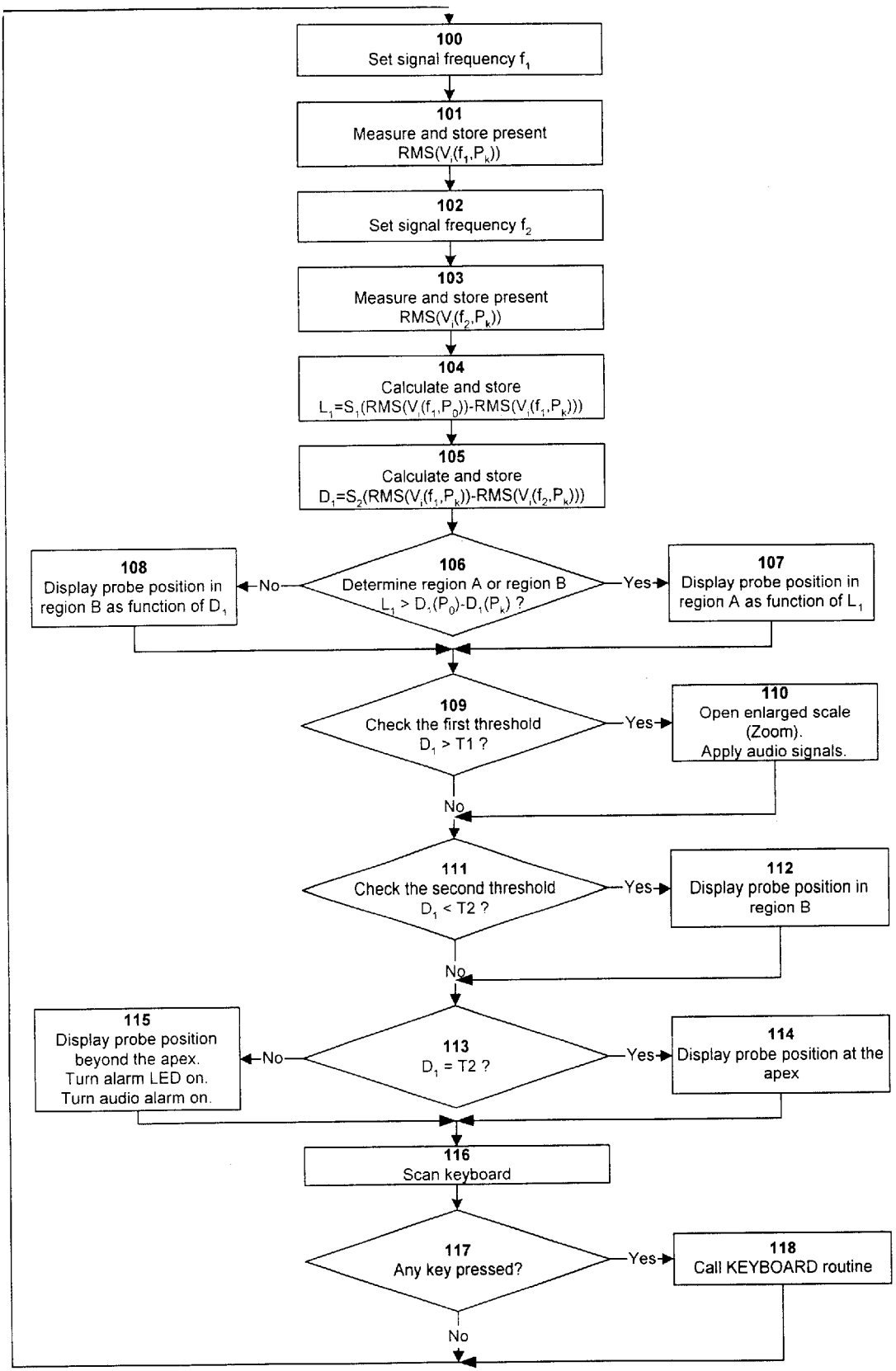
FIG. 4 is a flow chart of the steps and control paths for determining probe tip position inside a tooth canal and for visual and audio indication of the position according to one embodiment of the invention.

The steps for detecting the advance of the probe 5 inside regions A and B of the root canal 24 and in accordance with a preferred embodiment of the invention using two frequencies are shown in the flow chart of FIG. 4. The operation begins in step 100 with generation of an AC voltage having a predefined frequency $f_1$. The test voltage is then applied to the lip electrode 6 and the probe 5. Next, in step 101, the microcontroller 2 monitors the RMS of $V_i$ 22 through the amplifier 7, the RMS-to-DC converter 8 and the analog-to-digital converter (ADC) 9, and stores the data in memory 14. The ADC 9 continuously provides to the microcontroller 2 a digital signal representing the RMS that depends upon the probe voltages $V_i$. In step 102, under the control of the microcontroller 2, the signal generator 3 generates another AC voltage with predefined frequency $f_2$. In step 103 the microcontroller 2 monitors the second RMS value similarly to the step 101 and stores the second value in memory 14. In steps 104 and 105 the microcontroller 2 evaluates the test scores $L_1$ and $D_1$ respectively and stores the resulting values in memory 14.

Once the test scores have been calculated, in step 106 the software checks whether a predefined condition is fulfilled and determines whether the probe tip 25 is in the region A 31 or the region B 32. If $L_1 > D_1 (P_k) - D_1(P_0)$, the probe tip 25 is in the region A 31, and the software determines the location of probe tip 25 in the canal 24 from the value of the test function $L_1$ stored in the memory 14, and updates the display (step 107). Otherwise the probe tip is in the region B 32, and the software determines the location of probe tip 25 in canal 24 from the value of the test function $D_1$ stored in the memory 14, and updates the display (step 108). In step 109 the test score $D_1$ is compared to the first threshold value T1. If the test score exceeds the first threshold value T1, the probe tip 25 is close to the apex 26, and this is indicated to the user by means of the display 10 and/or audio transducer 11. In step 110 an enlarged image of the apex area is displayed on the display 10, and audio transducer is turned on. The controller then compares the test score $D_1$ to the second threshold value T2 (step 111). If the score $D_1$ does not exceed T2, the probe tip 25 has not yet reached the apex. The exact distance from the probe tip to the apex is determined by microcontroller 2 from the value of the test function $D_1$ stored in the memory 14, and the precise probe tip location is displayed on the enlarged scale on display 10. In step 113 the test score $D_1$ is further compared to the second threshold value T2. If $D_1$ is equal to the second threshold value T2, the probe tip is at the apex, and this is indicated to the user (step 114) by means of the display 10 and/or audio indicator 11. As shown in FIG. 3, the graphical display indicates the current location of probe tip 25 inside the canal 24 of a tooth in the region A 31 and in the region B 32. Alternatively, the position of the probe tip 25 may be presented numerically by a digital display or any other suitable indicating device.

If $D_1$ exceeds T2 (negative results at both steps 111 and 113), the probe tip 25 is beyond the apex and this is indicated to the user by means of visual and audio alarms (step 115).

In step 117 the input interface (keyboard 12) is scanned by the software. Once the interface routine (step 118) is complete, the software returns to step 100 to continue the measurements and display the results.

Figure 5:
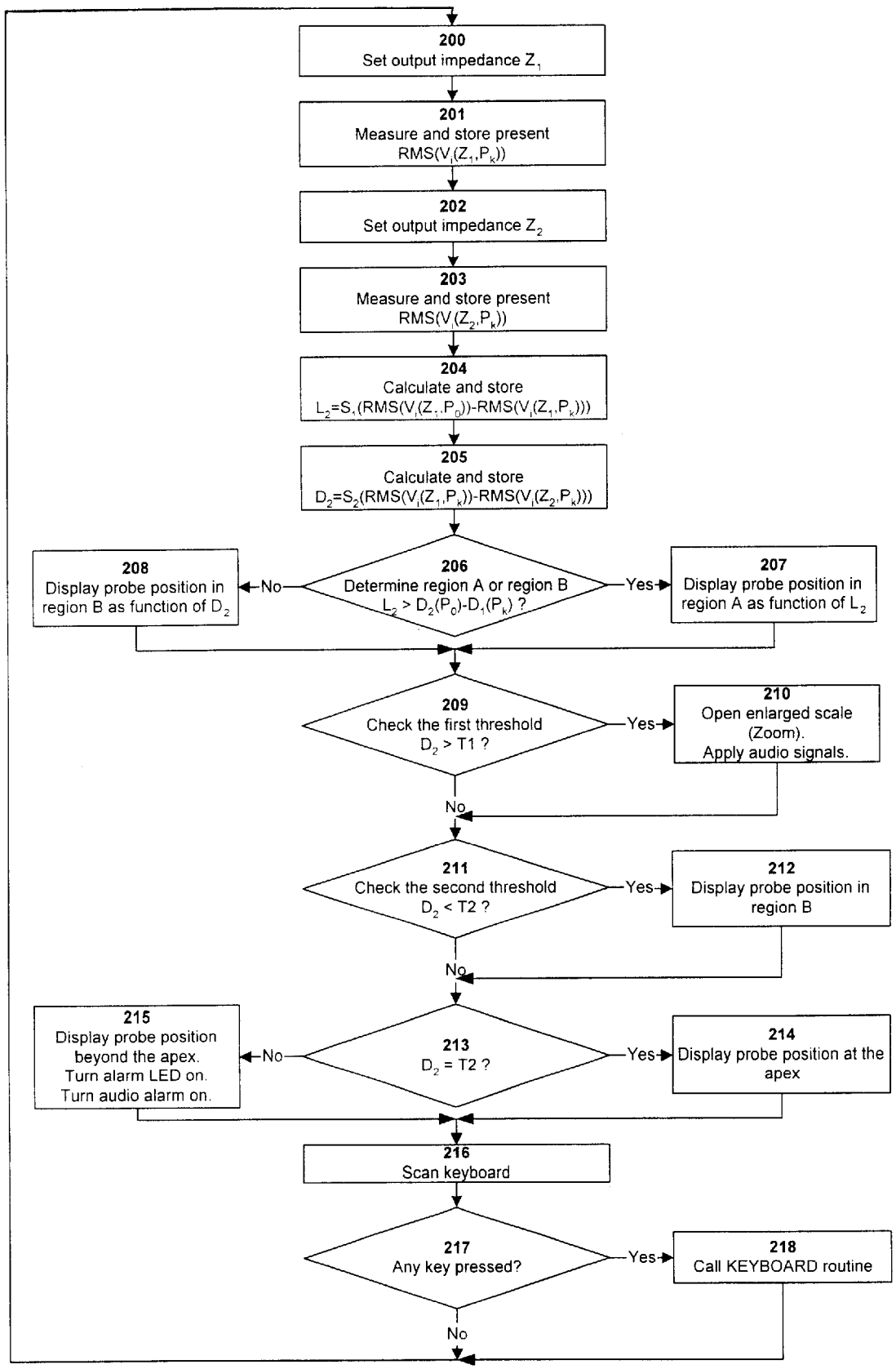
FIG. 5 is a flow chart of the steps and control paths for determining probe tip position inside a tooth canal and for visual and audio indication of the position according to another embodiment of the invention.

The steps for detecting the advance of the probe 5 inside regions A and B of the root canal 24 and in accordance with another preferred embodiment of the invention using two impedances are shown in the flow chart of FIG. 5. In this embodiment either the output impedance 21 of the driver 4 (FIG. 1) or the input impedance 30 of the input interface 17 (FIG. 2) is made to vary under the control of the microcontroller 2. The operation begins in step 200 with generation of an AC voltage while the variable impedance is set to $Z_1$. The test voltage is then applied to the lip electrode 6 and the probe 5. Next, in step 201, the microcontroller 2 monitors the RMS of $V_1$ 22 through the amplifier 7, the RMS-to-DC converter 8 and the analog-to-digital converter (ADC) 9, and stores the data in memory 14. The ADC 9 continuously provides to the microcontroller 2 a digital signal representing the RMS that depends upon the probe voltages $V_i$. In step 202, under the control of the microcontroller 2, the signal generator 3 generates the same AC voltage with the variable impedance set to $Z_2$. In step 203 the microcontroller 2 monitors the second RMS value similarly to the step 201 and stores the second value in memory 14. In steps 204 and 205 the microcontroller 2 evaluates the test scores $L_2$ and $D_2$ respectively and stores the resulting values in memory 14.

Once the test scores have been calculated, in step 206 the software checks whether a predefined condition is fulfilled and determines whether the probe tip 25 is in the region A 31 or the region B 32. For example, if $L_2>D_2(P_k)-D_2(P_0)$, the probe tip 25 is in the region A 31, and the software determines the location of probe tip 25 in the canal 24 from the value of the test function $L_2$ stored in the memory 14, and updates the display (step 207). Otherwise the probe tip 25 is in the region B 32, the software determines the location of probe tip 25 in canal 24 from the value of the test function $D_2$ stored in the memory 14 and updates the display (step 208). In step 209 the test score $D_2$ is compared to the first threshold value T1. If the test score exceeds the first threshold value T1, the probe tip 25 is close to the apex 26, and this is indicated to the user by means of the display 10 and/or audio transducer 11. In step 210 an enlarged image of the apex area is displayed on the display 10, and audio transducer is turned on. The controller then compares the test score $D_2$ to the second threshold value n (step 211). If the score $D_2$ does not exceed T2, the probe tip 25 has not yet reached the apex. The exact distance from the probe tip to the apex is determined by microcontroller 2 from the value of the test function $D_2$ stored in the memory 14, and the precise probe tip location is displayed on the enlarged scale on display 10. In step 213 the test score $D_2$ is further compared to the second threshold value T2. If $D_2$ is equal to the second threshold value T2, the probe tip is at the apex, and this is indicated to the user (step 214) by means of the display 10 and/or audio indicator 11. As shown in FIG. 3, the graphical display indicates the current location of probe tip 25 inside the canal 24 of a tooth in the region A 31 and in the region B 32. Alternatively, the position of the probe tip may be presented numerically by a digital display or any other suitable indicating device.

If $D_2$ exceeds T2 (negative results at both steps 211 and 213), the probe tip 25 is beyond the apex 27 and this is indicated to the user by means of visual and audio alarms (step 215).

In step 217 the keyboard 12 is scanned by the software. Once the interface routine (step 218) is complete, the software returns to step 200 to continue the measurements and display the results.

What is claimed is:

1. A device for locating an apex of a root canal of a tooth, the root canal having a region A and a region B, comprising:
   a a first electrode, the first electrode including a conductive probe having a probe tip and being adapted for insertion into the root canal;
   b a second electrode configured to electrically contact a patient's body;
   c an AC voltage generator configured to provide an AC test voltage signal Vg having one or more frequencies;
   d an AC voltage driver being an interface between the voltage generator and the electrodes, the voltage driver having an internal output impedance,
   e a voltage detector coupled to the first and second electrodes, the voltage detector having an input impedance and being operative to detect an AC voltage Vi across the first and second electrodes;
   f an electronic controller coupled to the voltage detector, the controller carrying out the steps of:
      fa calculating one or more test scores, wherein at least one of test scores involves an algorithmic expression involving RMS(Vi(f)), wherein f is a frequency of Vg:
      fb determining, on the basis of said one or more test score values, a position of the probe tip in the canal; and
      fc informing a user of the position of the probe tip in the canal.

2. The device of claim 1 wherein $V_g$ has a single frequency.

3. The device of claim 1 wherein $V_g$ has two or more frequencies or alternates between two frequencies.

4. The device of claim 1 wherein $V_g$ has two frequencies or $V_g$ alternates between two frequencies.

5. The device of claim 3 wherein one or more of the frequencies is changed when one or more of the test scores satisfy a predetermined condition.

6. The device of claim 4 wherein at least one of the one or more test scores involves an algorithmic expression involving the $RMS(V_i(f_1))$ and $RMS(V_i(f_2))$ wherein $f_1$ and $f_2$ are the two frequencies of $V_g$ or the two frequencies between which $V_g$ alternates.

7. The device of claim 6 wherein the at least one of the one or more test scores involves an algorithmic expression involving $RMS(V_i(f_1))-RMS(V_i(f_2))$ or $RMS(V_i(f_1))/RMS(V_i(f_2))$.

8. The device of claim 1 wherein a $V_g$ has a first frequency $f_1$ and a second frequency $f_2$ or alternates between two frequencies $f_1$ and $f_2$;

b a first test score involves an algorithmic expression involving the $RMS(f_1)$, the first test score being used to locate the probe tip when the probe tip is in the region A of the root canal; and c a second test score involves an algorithmic expression involving $RMS(V_i(f_1))-RMS(V_i(f_2))$, the second test score being used to locate the probe tip when the probe tip is in the region B of the root canal.

9. The device of claim 8 wherein the first test score is $L_1$ and the second test score is $D_1$.

10. The device of claim 1 wherein the internal output impedance of the voltage driver is constant.

11. The device of claim 10 wherein at least one of the one or more test scores involves an algorithmic expression involving the $RMS(V_i(Z))$, wherein Z is the internal output impedance of the voltage driver.

12. The device of claim 1 wherein the internal output impedance of the voltage driver alternates between two or more values.

13. The device of claim 1 wherein the internal output impedance of the voltage driver alternates between two values.

14. The device of claim 13 wherein at least one of the one or more test scores involves an algorithmic expression involving the $RMS(Z_1)$ or $RMS(Z_2)$ wherein $Z_1$ and $Z_2$ are the two impedances between which the internal output impedance alternates.

15. The device of claim 14 wherein at least one of the one or more test scores involves an algorithmic expression involving $RMS(V_i(Z_1))-RMS(V_i(Z_2))$ or, $RMS(V_i(Z_1))/RMS(V_i(Z_2))$.

16. The device of claim 14 wherein a the internal output impedance of the voltage driver alternates between two impedance values;

b a first test score involves an algorithmic expression involving the $RMS(Z_1)$, the first test score being used to locate the probe tip in the root canal when the probe tip is in the region A; and c a second test score involves an algorithmic expression involving $RMS(V_i(Z_1))-RMS(V_1(Z_2))$, the second test score being used to locate the probe tip when the probe tip is in the region B.

17. The device of claim 16 wherein the first test score is $L_2$ and the second test score is $D_2$.

18. The device of claim 1 wherein the input impedance of the voltage detector is constant.

19. The device of claim 18 wherein at least one of the one or more test scores involves an algorithmic expression involving the $RMS(V_i(Z))$, wherein Z is the input impedance of the voltage detector.

20. The device of claim 1 wherein the input impedance of the voltage detector alternates between two or more values.

21. The device of claim 20 wherein the input impedance of the voltage detector alternates between two values.

22. The device of claim 21 wherein at least one of the one or more test scores involves an algorithmic expression involving the $RMS(Z_1)$ and $RMS(Z_2)$ wherein $Z_1$ and $Z_2$ are the two impedances between which the input impedance alternates.

23. The device of claim 22 wherein the at least one of the one or more test scores involves an algorithmic expression involving $RMS(V_i(Z_1))-RMS(V_i(Z_2))$ or, $RMS(V_i(Z_i))/RMS(V_i(Z_2))$.

24. The device of claim 23 wherein a the input impedance of the voltage detector alternates between two impedance values;

b a first test score involves an algorithmic expression involving the $RMS(Z_1)$, the first test score being used to locate the probe tip in the root canal when the probe tip is in the region A; and c a second test score involves an algorithmic expression involving $RMS(V_i(Z_1))-RMS(V_i(Z_2))$, the second test score being used to locate the probe tip when the probe tip is in the region B.

25. The device of claim 24 wherein the first test score is $L_2$ and the second test score is $D_2$.

26. The device of claim 1 wherein the step of determining, the position of the probe tip in the canal includes one or more of the following steps:

a determining whether one or more of the test scores satisfies a first predetermined condition, one or more of the test scores satisfying the predetermined condition being indicative of the probe tip being in the region A, b determining whether one or more of the test scores satisfies a second predetermined condition, one or more of the test scores satisfying the second predetermined condition being indicative of the probe tip being in the region B;

c determining whether one or more of the test scores satisfies a third predetermined condition, one or more of the test scores satisfying the third predetermined condition being indicative of the probe tip being at the apex; and d determining whether one or more of the test scores satisfies a fourth predetermined condition, one or more of the test scores satisfying the fourth predetermined condition being indicative of the probe tip having passed the apex and entered jaw tissue.

27. The device of claim 1 further comprising a display.

28. The device of claim 27 wherein the display includes one or more illustrations of a tooth or a part thereof.

29. The device of claim 28 wherein the step of informing a user of the position of the probe tip in the canal includes introducing into the illustration on the display a marker, the position of the marker in the display being dependent upon the position of the probe tip in the canal.

30. The device of claim 29 wherein the display includes an illustration of a region A of a tooth canal and an illustration of an apex of a root canal, and the step of informing a user of the position of the probe tip in region A of the canal includes introducing into the illustration of region A on the display a marker, the position of the marker in the display being dependent upon the position of the probe tip in region A, and the step of informing a user of the position of the probe tip in region B of the canal includes introducing into the illustration of region B on the display a marker, the position of the marker in the display being dependent upon the position of the probe tip in region B.

31. The device of claim 21 wherein the display is a digital display.

32. The device of claim 31 wherein the step of informing a user of the position of the probe tip in the canal includes displaying a number in the digital display, the number depending upon the position of the probe tip in the canal.

33. The device of claim 1 further comprising an audio transducer.

34. The device of claim 33 wherein the step of informing a user of the position of the probe tip in the canal includes producing an audible sound, the sound being indicative of the position of the probe tip in the canal.

35. A device for locating an apex of a root canal of a tooth, the root canal having a region A and a region B, comprising:
 a a first electrode, the first electrode including a conductive probe with a probe tip, the probe being adapted for insertion into the root canal;
 b a second electrode configured to electrically contact a patient's body;
 c an AC voltage generator configured to provide an AC test voltage signal Vg;
 d an AC voltage driver being an interface between the voltage generator and the electrodes, the driver having an internal output impedance;
 e a voltage detector coupled to the first and second electrodes, the voltage detector having an input impedance and being operative to detect an AC voltage Vi across the first and second electrodes;
 f an electronic controller coupled to the voltage detector, the controller carrying out the steps of:
  fa calculating one or more test scores, the one or more test scores each having a value that is a function of Vi;
  fb determining, on the basis of said one or more test score values, a position of the probe tip in the canal; and
  fc informing a user of the position of the probe tip in the canal,
wherein at least one of the internal output impedance and the input impedance alternates between two or more values.

36. The device of claim 35, wherein Vg has two or more frequencies or alternates between three or more frequencies.

37. The device according to claim 35, wherein Vg has two frequencies or Vg alternates between two frequencies.

38. The device according to claim 35, wherein Vg has two or more frequencies or alternates between two or more frequencies, and wherein one or more frequencies changes when one or more of the test scores satisfies a predetermined condition.

39. The device of claim 35, wherein the internal output impedance of the voltage driver alternates between two or more values.

40. The device of claim 35, wherein the internal output impedance of the voltage driver alternates between two values.

41. The device of claim 35, wherein the step of determining the position of the probe tip in the canal includes one or more of the following sub-steps:
 a determining whether one or more of the test scores satisfies a first predetermined condition, one or more of the test scores satisfying the predetermined condition being indicative of the probe tip being in the region A;
 b determining whether one or more of the test scores satisfies a second predetermined condition, one or more of the test scores satisfying the second predetermined condition being indicative of the probe tip being in the region B;
 c determining whether one or more of the test scores satisfies a third predetermined condition, one or more of the test scores satisfying the third predetermined condition being indicative of the probe tip being at the apex; and
 d determining whether one or more of the test scores satisfies a fourth predetermined condition, one or more of the test scores satisfying the fourth predetermined condition being indicative of the probe tip having passed the apex and entered jaw tissue.

42. The device of claim 35, further comprising a display.

43. The device of claim 42, wherein the display includes one or more illustrations of the tooth or a part thereof.

44. The device of claim 43, wherein the step of informing the user of the position of the probe tip in the canal includes introducing into the illustration on the display a marker, a position of the marker on the display being dependent upon the position of the probe tip in the canal.

45. The device of claim 44, wherein the display includes an illustration of the region A of the root canal of the tooth and an illustration of the apex of the root canal, and the step of informing the user of the position of the probe tip in the region A of the canal includes introducing into the illustration of the region A on the display a marker, a position of the marker on the display being dependent upon the position of the probe tip in region A, and the step of informing the user of the position of the probe tip in the region B of the canal includes introducing into the illustration of region B on the display a marker, a position of the marker on the display being dependent upon the position of the probe tip in region B.

46. The device of claim 42, wherein the display is a digital display.

47. The device of claim 46, wherein the step of informing the user of the position of the probe tip in the canal includes displaying a number on the digital display, the number depending upon the position of the probe tip in the canal.

48. The device of claim 35 further comprising an audio transducer.

49. The device of claim 48, wherein the step of informing the user of the position of the probe tip in the canal includes producing an audible sound, the sound being indicative of the position of the probe tip in the canal.

50. A device for locating an apex of a root canal of a tooth, the root canal having a region A and a region B, comprising:
 a a first electrode, the first electrode including a conductive probe with a probe tip, the probe being adapted for insertion into the root canal;
 b a second electrode configured to electrically contact a patient's body;
 c an AC voltage generator configured to provide an AC test voltage signal Vg having one or more frequencies;
 d an AC voltage driver being an interface between the voltage generator and the electrodes, the driver having an internal output impedance;
 e a voltage detector coupled to the first and second electrodes, the voltage detector having an input impedance and being operative to detect an AC voltage Vi across the first and second electrodes;
 f an electronic controller coupled to the voltage detector, the controller carrying out the steps of:
  fa calculating one or more test scores, the one or more test scores each having a value that is a function of Vi;
  fb determining, on the basis of the one or more test score values, a position of the probe tip in the canal; and
  fc informing a user of the position of the probe tip in the canal, wherein Vg has two or more frequencies or alternates between two or more frequencies and wherein one or more of the frequencies changes when one or more or the test scores satisfies a predetermined condition.

51. The device of claim 50, wherein the internal output impedance of the voltage driver alternates between two or more values.

52. The device of claim 50, wherein the internal output impedance of the voltage driver alternates between two values.

53. The device of claim 50, wherein the step of determining the position of the probe tip in the canal includes one or more of the following sub-steps:

a determining whether one or more of the test scores satisfies a first predetermined condition, one or more of the test scores satisfying the predetermined condition being indicative of the probe tip being in the region A;

b determining whether one or more of the test scores satisfies a second predetermined condition, one or more of the test scores satisfying the second predetermined condition being indicative of the probe tip being in the region B;

c determining whether one or more of the test scores satisfies a third predetermined condition, one or more of the test scores satisfying the third predetermined condition being indicative of the probe tip being at the apex; and d determining whether one or more of the test scores satisfies a fourth predetermined condition, one or more of the test scores satisfying the fourth predetermined condition being indicative of the probe tip having passed the apex and entered jaw tissue.

54. The device of claim 50, further comprising a display.

55. The device of claim 54, wherein the display includes one or more illustrations of the tooth or a part thereof.

56. The device of claim 55, wherein the step of informing the user of the position of the probe tip in the canal includes introducing into the illustration on the display a marker, a position of the marker on the display being dependent upon the position of the probe tip in the canal.

57. The device of claim 56, wherein the display includes an illustration of the region A of the root canal of the tooth and an illustration of the apex of the root canal, and the step of informing a user of the position of the probe tip in the region A of the canal includes introducing into the illustration of the region A on the display a marker, the position of the marker on the display being dependent upon the position of the probe tip in region A, and the step of informing the user of the position of the probe tip in the region B of the canal includes introducing into the illustration of region B on the display a marker, the position of the marker on the display being dependent upon the position of the probe tip in region B.

58. The device of claim 54, wherein the display is a digital display.

59. The device of claim 58, wherein the step of informing the user of the position of the probe tip in the canal includes displaying a number on the digital display, the number depending upon the position of the probe tip in the canal.

60. The device of claim 50, further comprising an audio transducer.

61. The device of claim 60, wherein the step of informing the user of the position of the probe tip in the canal includes producing an audible sound, the sound being indicative of the position of the probe tip in the canal.

* * * * *